US009387106B2

(12) United States Patent  
Stante et al.

(10) Patent No.: US 9,387,106 B2  
(45) Date of Patent: Jul. 12, 2016

(54) MEDICAL DEVICE DELIVERY SYSTEMS AND METHODS OF USE THEREOF

(71) Applicant: Medtronic Vascular, Inc., Santa Rosa, CA (US)

(72) Inventors: Glenn Stante, Santa Rosa, CA (US); Shishira Nagesh, Santa Rosa, CA (US); Billy Tam, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 163 days.

(21) Appl. No.: 13/780,634

(22) Filed: Feb. 28, 2013

(65) Prior Publication Data

US 2014/0243953 A1 Aug. 28, 2014

(51) Int. Cl.
*A61F 2/06* (2013.01)
*A61F 2/966* (2013.01)
*A61F 2/24* (2006.01)

(52) U.S. Cl.
CPC .............. *A61F 2/966* (2013.01); *A61F 2/2433* (2013.01); *A61F 2002/9665* (2013.01); *A61F 2250/0098* (2013.01)

(58) Field of Classification Search
CPC .................. A61B 19/22; A61F 2/2433; A61F 2002/9665
USPC .................................. 623/2.11, 2.18; 606/108
See application file for complete search history.

(56) References Cited

U.S. PATENT DOCUMENTS

| | | | |
|---|---|---|---|
| 5,429,617 A * | 7/1995 | Hammersmark . | A61M 25/0108 600/435 |
| 5,759,174 A | 6/1998 | Fischell et al. | |
| 6,554,848 B2 | 4/2003 | Boylan et al. | |
| 6,858,034 B1 * | 2/2005 | Hijlkema ................. | A61F 2/95 606/108 |
| 7,641,647 B2 | 1/2010 | Gunderson | |
| 8,206,427 B1 * | 6/2012 | Ryan ........................ | A61F 2/07 623/1.11 |
| 2001/0049549 A1 * | 12/2001 | Boylan ..................... | A61F 2/95 623/1.11 |
| 2002/0029079 A1 * | 3/2002 | Kim et al. ..................... | 623/1.25 |
| 2003/0009174 A1 * | 1/2003 | Smith ..................... | A61F 2/966 606/108 |
| 2003/0153968 A1 * | 8/2003 | Geis .......................... | A61F 2/07 623/1.11 |
| 2004/0006381 A1 * | 1/2004 | Sequin .................... | A61F 2/915 623/1.12 |
| 2004/0204749 A1 * | 10/2004 | Gunderson ............... | A61F 2/91 623/1.12 |
| 2005/0148866 A1 * | 7/2005 | Gunderson ....... | A61M 25/0012 600/431 |
| 2006/0009833 A1 | 1/2006 | Chobotov et al. | |
| 2006/0253186 A1 * | 11/2006 | Bates .......................... | 623/1.11 |
| 2007/0049549 A1 * | 3/2007 | Nelson ................. | A61K 38/193 514/44 R |
| 2009/0076584 A1 * | 3/2009 | Mao et al. ..................... | 623/1.11 |
| 2010/0100167 A1 | 4/2010 | Bortlein et al. | |

FOREIGN PATENT DOCUMENTS

EP 0782841 7/1997

OTHER PUBLICATIONS

PCT/US2014/016937, PCT International Search Report and Written Opinion, mailed Jun. 4, 2014.

* cited by examiner

*Primary Examiner* — Richard Louis

(57) ABSTRACT

A delivery system for delivering a medical device through a vasculature can include a capsule for housing the medical device during delivery and a marker band rotatably fixed to the capsule. The marker band can include a band portion and a single indicator protruding from the band portion. The indicator can allow the rotational orientation of the marker band to be determined while the medical device is in the vasculature, the rotational orientation being around a central axis of the vasculature. A delivery system for delivering a medical device through a vasculature includes a capsule for housing the medical device during delivery and a marker band attached to a proximal end of the capsule. The marker band can include a base portion and a protrusion that can be configured to extend from the base portion towards a distal end of the capsule. Related methods are also described.

14 Claims, 16 Drawing Sheets

MEDICAL DEVICE DELIVERY SYSTEMS AND METHODS OF USE THEREOF

BACKGROUND

1. Field

Certain embodiments of the present invention are related to medical device delivery systems and methods of using the system.

2. Background Art

Existing medical device delivery systems, such as those for use in percutaneous medical procedures, can allow a medical device to be delivered through a patient's vasculature to a delivery site where it can be implanted within a patient. In some procedures a medical device in the form of a valve prosthesis can be compacted and loaded onto a delivery device for advancement through a patient's vasculature in a transfemoral, transapical, and/or transatrial procedure. There is a continuous need for improved delivery systems for use in percutaneous and other delivery techniques.

BRIEF SUMMARY

In some situations, it can be desirable to improve consistency and predictability of delivery systems. These improvements can, for example, result in decreased operation time as well as more accurate positioning. Due to the tortuosity of a given patient's native anatomy, the process of tracking a delivery system therethrough can often result in an undesirable rotation of the system. In some delivery procedures, the rotation of the delivery system can be especially important.

In some embodiments, a delivery system can include an indicator at a distal end of the delivery system that can allow confirmation of the correct orientation of the medical device (such as the correct orientation of a valve with respect to native leaflets) without first deploying the medical device. For example, the orientation of the medical device can be determined during tracking up to the aorta via a fluoroscopic view of the marker band. If the medical device is in an undesired orientation, the delivery system can be retracted and/or adjusted to a desired orientation.

In some embodiments, a delivery system for delivering a medical device through a vasculature can include a capsule for housing the medical device during delivery and a marker band rotatably fixed to the capsule. The marker band can include a band portion and a single indicator protruding from the band portion. The indicator can be configured to allow the rotational orientation of the marker band to be determined while the medical device is in the vasculature. The rotational orientation, can for example be relative to a central axis of the vasculature.

A method for determining a rotational orientation of a delivery system for a medical device through a vasculature can include providing a delivery system including a capsule and a marker band rotatably fixed to the capsule, the marker band including an indicator configured to allow rotational orientation of the marker band to be determined while the capsule is in the vasculature. The method can further include delivering the medical device through the vasculature and determining a rotational orientation of the marker band while the capsule is in the vasculature.

In some embodiments, a delivery system for delivering a medical device through a vasculature includes a capsule for housing the medical device during delivery and a marker band attached to a proximal end of the capsule. In some embodiments, the marker band is attached to a distal end or an intermediate portion of the capsule. The marker band can include a base portion and a protrusion that can be configured to extend from the base portion towards a distal end of the capsule. In some embodiments, the protrusion can protrude towards a proximal end of the capsule.

BRIEF DESCRIPTION OF THE DRAWINGS/FIGURES

The accompanying figures, which are incorporated herein, form part of the specification and illustrate embodiments of relevant delivery systems and related methods. Together with the description, the figures further serve to explain the principles of and to enable a person skilled in the relevant art(s) to make and use the systems described herein.

DETAILED DESCRIPTION

The following detailed description refers to the accompanying figures which illustrate several embodiments. Other embodiments are possible. Modifications can be made to the embodiments described herein without departing from the spirit and scope of the present invention. Therefore, the following detailed description is not meant to be limiting.

Figure 1:
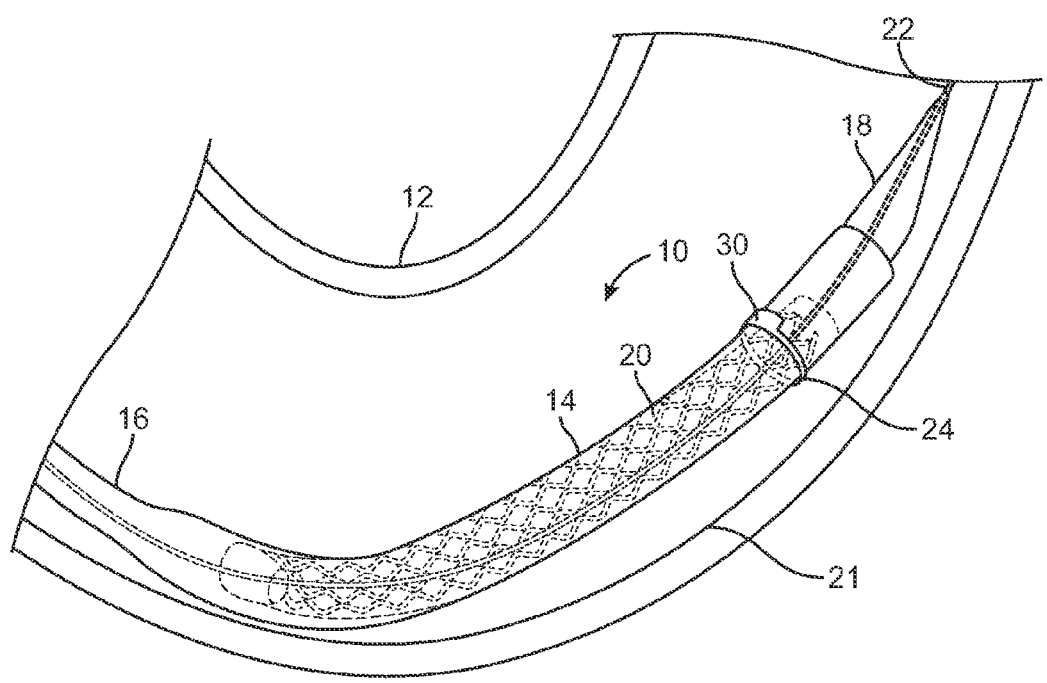
FIG. 1 illustrates a delivery system in accordance with one embodiment of the present invention within a vasculature.

FIG. 1 illustrates a delivery system 10 that can, for example, be used to deliver a medical device through a patient's vasculature 12 or a simulated vasculature. Delivery system 10 includes a capsule 14, sheath 16, dilator 18, medical device 20, and guide wire 22. In some embodiments, medical device 20 can be in the form of a prosthetic heart valve including a frame attached to a valve body. In some embodiments, the valve body can be formed, for example, from one or more of biocompatible synthetic materials, synthetic polymers, autograft tissue, homograft tissue, xenograft tissue, or one or more other suitable materials. In some embodiments, the valve body can be formed, for example, from bovine, porcine, equine, ovine, and/or other suitable animal tissues. In some embodiments, the valve body can be formed, for example, from heart valve tissue, pericardium, and/or other suitable tissue. In some embodiments, the valve body can comprise one or more valve leaflets, such as for example, a tri-leaflet bovine pericardium valve, a bi-leaflet valve, or another suitable valve.

Suitable medical devices for use in system 10 are not limited to prosthetic heart valves. In some embodiments, medical device 20 can be a device configured to be transported via a delivery catheter. In some embodiments, medical device 20 can be an expandable device, such as, for example, a percutaneously delivered device configured to be compacted and loaded onto a delivery catheter for advancement through a natural or artificial body lumen, such as for example through a patient's vasculature. In some embodiments, medical device 20 is not expandable. In some embodiments, medical device 20 is not designed to be implanted within the patient's body. For example, medical device 20 can be an embolic filter or a tool for retrieving an item from inside a patient.

In some embodiments, system 10 can be used in one or more percutaneous delivery procedures. For example, in some percutaneous procedures, a valve prosthesis can be compacted and loaded onto a delivery device, such as for example a catheter, for advancement through a patient's vasculature. System 10 can be configured for use in illiofemoral, apical, radial, direct aortic, and subclavian/axillary entry locations. System 10 can be configured to allow access from multiple locations per procedure (e.g. bilateral femoral access). In some embodiments, system 10 can be configured to deliver medical device 20 through an artery or vein, a femoral artery, a femoral vein, a jugular vein, a subclavian artery, an axillary artery, an aorta, an atrium, and/or a ventricle. System 10 can be configured to deliver medical device 20 via a transfemoral, transapical, transseptal, transatrial, transventrical, or transaortic procedure. In some embodiments, one or more components or portion of components of system 10 can be configured to flex to facilitate the traversal of system 10 through a body lumen during a delivery procedure. In some embodiments, one or more components of system 10 or portions thereof can include a curved outer surface and/or shape to facilitate movement through a curved body lumen.

As described above, in some embodiments, system 10 can be configured for use in a transfemoral delivery procedure. In one example of such a procedure, a delivery device including a prosthetic heart valve can be advanced in a retrograde manner through a patient's femoral artery and into the patient's descending aorta. A catheter can then be advanced under fluoroscopic guidance over the simulated aortic arch, through the ascending aorta, into the left ventricle, and mid-way across the defective aortic valve. Once positioning of the catheter is confirmed, the valve prosthesis can be deployed within the valve annulus. The valve prosthesis can then expand against the simulated annulus. In some embodiments, as the valve prosthesis is expanded, it can trap leaflets against the annulus, which can retain the native valve in a permanently open state.

As described above, in some embodiments, system 10 can be configured for use in a transapical delivery procedure. In one example of such a procedure, a trocar or overtube can be inserted into a patient's left ventricle through an incision created in the apex of the patient's heart. A dilator can be used to aid in the insertion of the trocar. In this approach, the native valve (for example, the mitral valve) can be approached downstream relative to blood flow. The trocar can be retracted sufficiently to release the self-expanding valve prosthesis. The dilator can be presented between the leaflets. The trocar can be rotated and adjusted to align the valve prosthesis in a desired alignment. The dilator can be advanced into the left atrium to begin disengaging the proximal section of the valve prosthesis from the dilator.

In some embodiments, system 10 can be configured for use in a transatrial delivery procedure. In one example of such a procedure, a dilator and trocar can be inserted through an incision made in the wall of the left atrium of the heart. The dilator and trocar can then be advanced through the native valve and into the left ventricle of the heart. The dilator can then be withdrawn from the trocar. A guide wire can be advanced through the trocar to the point where the valve prosthesis comes to the end of the trocar. The valve prosthesis can be advanced sufficiently to release a self-expanding valve prosthesis from the trocar. The trocar can be rotated and adjusted to align the valve prosthesis in a desired alignment. The trocar can be withdrawn completely from the heart such that the valve prosthesis self-expands into position and can assume the function of the native valve.

The few example procedures described above are not intended to be exhaustive. It is understood that not every act need be performed and additional acts can be included as would be apparent to one of ordinary skill in the art. In addition, the acts can be reordered as desired. Other medical devices and delivery techniques can be used with any of the parts described herein. It is further understood that the above delivery routes are merely exemplary and that other suitable delivery routes can be employed. The terms "delivery" and "delivery system" as used herein is intended to refer broadly to positioning a medical device at a desired location and related systems. Such terms do not necessitate a system that actually deposits a medical device at a site, such as for example a device that can be used to implant a prosthetic heart valve. The term "delivery system" can cover, for example, a system that temporarily positions a medical device at a desired location. For example, the delivery system can be used to position an embolic filter at a desired location within a patient's vasculature for a period of time before removing the embolic filter.

As described above, delivery system 10 can include dilator 18. In some embodiments, dilator 18 can be configured to dilate a tube, cavity, and/or opening in the body to facilitate introduction of system 10 for a delivery procedure. In some embodiments, dilator 18 can be configured to facilitate removal of system 10 following delivery of medical device 20.

Capsule 14 can be configured to house medical device 20 for delivery via system 10. For example, capsule 14 can include a lumen that is configured to receive the entirety of medical device 20 or a portion thereof. Capsule 14 can be in the form of a tube or another suitable shape. In some embodiments, capsule 14 can be in the form of a sheath. In some embodiments, a portion of capsule 14 can be tapered. For example, one or both of a proximal and a distal end of capsule 14 can be tapered. In some embodiments, capsule 14 can be a split sheath, such as one or more of the split sheath configurations described for example in U.S. Publication Appl. No. 2010/0100167, the disclosure of which is incorporated in its entirety by reference thereto.

Capsule 14 can include a marker band 24. Marker band 24 can, for example, be rotatably fixed to capsule 14. As described further herein, marker band 24 can include an indicator 30 that allows rotational orientation of the marker band to be determined while the medical device is in the vasculature. In some embodiments, an axial rotation of system 10 can additionally or alternatively be determined using marker band 24. For example, as shown in FIG. 1, the distal end of system 10 is angled in a direction away from the viewer. This angle is indicated by the profile of the band portion of marker band 24. For example, as shown in FIG. 1, the profile of the band portion is substantially oval shaped, which indicates that marker band 24 is at an angle towards or away from the viewer. If the profile of the band portion of marker band 24 is a straight line instead of an oval, then a viewer can conclude that marker band 24 is not at an angle relative to the viewer.

Marker band 24 can, for example, be attached to a proximal end of capsule 14. When marker band 24 is positioned at a proximal end of capsule 14, the configuration can allow a user to determine when capsule 14 has been deployed far enough to get full release of medical device 20. Alternatively or additionally, marker band 24 can be positioned at a distal end of capsule 14. When marker band 24 is positioned at a distal end of capsule 14, the configuration can allow a user to know where the leading edge of capsule 14 is located. In some embodiments, marker band 24 can be positioned between a distal end and a proximal end of capsule 14.

As described above, due to the tortuosity of a given patient's native anatomy (such as within vasculature 12), the process of tracking delivery system 10 therethrough can often result in an undesirable rotation of medical device 20, capsule 14, and/or other components of system 10. In some delivery procedures, maintaining a desired rotation of these components can be especially important. A desired orientation of medical device 20 can be determined based on a number of factors. For example, in a tricuspid transcather aortic valve delivery procedure, it may be advantageous to deploy the valve with the same orientation as native leaflets. Further, when medical device 20 is in the form of a prosthetic heart valve, the following factors can be considered, alone or in combination, to verify that the valve is properly placed in an implantation site: (1) lack of paravalvular leakage around the replacement valve while blood is flowing through the valve; (2) orientation of the replacement valve relative to the coronary arteries; (3) the presence of coronary flow with the replacement valve in place; (4) longitudinal alignment of the replacement valve annulus with respect to the native patient anatomy; (5) verification that the position of the sinus region of the replacement valve does not interfere with native coronary flow; (6) verification that a sealing skirt is aligned with anatomical features to reduce and/or minimize paravalvular leakage; (7) verification that the replacement valve does not induce arrhythmias prior to final release; (8) verification that the replacement valve does not interfere with function of an adjacent valve, such as the mitral valve; (9) verification that engagement arms of the valve correspond to one or more sinus regions of the native anatomy; and (10) verification of desired rotational orientation for medical devices having asymmetrical profiles. By maintaining a desired rotation of medical device 20 relative to capsule 14 and/or other components of system 10, one or more of the above benefits can be achieved.

As shown for example in FIG. 1, as system 10 is tracked through vasculature 12, indicator 30 is oriented on an opposite side of capsule 14 from a curve 21 of vasculature 12. If desired, system 10 can be rotated in order to orient indicator 30 to face curve 21 or another direction.

Figure 2:
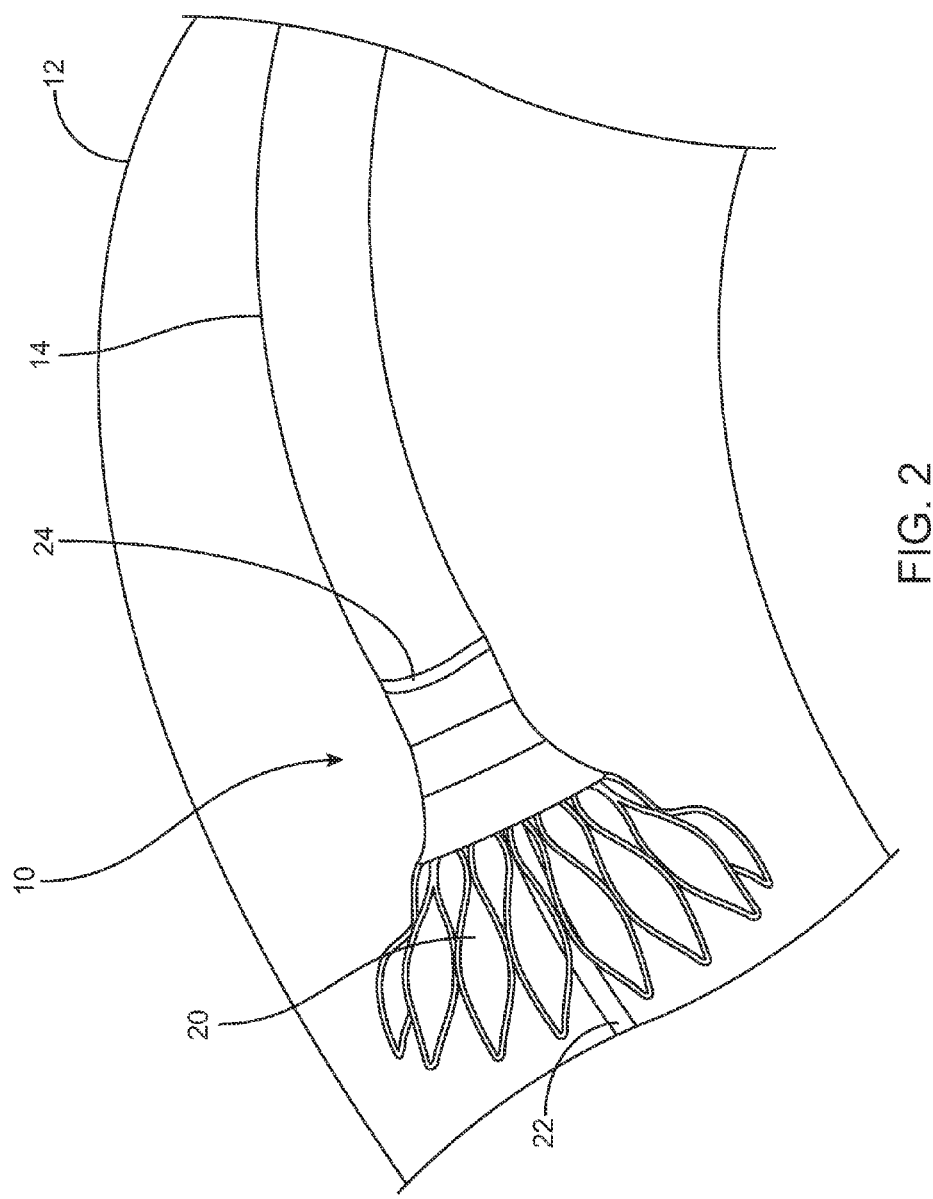
FIG. 2 illustrates the delivery system of FIG. 1 with a medical device housed therein partially released.

FIG. 2 illustrates system 10 with medical device 20 partially released. In some embodiments, as capsule 14 is retracted from medical device 20, medical device 20 can radially expand. In order to accommodate medical device 20, capsule 14 can therefore be configured to flare radially outwards in order to facilitate the release and/or recapture of medical device 20. In some embodiments, this flaring can lower the force on medical device 20 as it is being released or as it is being recaptured. Marker band 24 may be designed or positioned to allow capsule 14 to flare outwards. For example, if marker band 24 is in the form of a solid, non-expandable continuous ring, then marker band 24 may need to be positioned away from the distal end of capsule 14 in order to allow capsule 14 to flare outwards. In addition, one or more of indicators 30 can also be sized or positioned to allow capsule 14 to flare outwards.

In some embodiments, capsule 14 can be configured to move relative to medical device 20 to partially or fully release medical device 20 for delivery by system 10. In some embodiments, system 10 is configured to move capsule 14 relative to medical device 20 by moving capsule 14 from a first position to a second position while medical device 20 is relatively stationary. For example, in some embodiments, capsule 14 can be configured to move in a proximal direction relative to medical device 20 to partially or fully expose medical device 20 to allow for delivery medical device 20. In some embodiments, system 10 is configured to move capsule 14 relative to medical device 20 by moving medical device 20 from a first position to a second position while capsule 14 is relatively stationary. For example, medical device 20 can be pushed relative to capsule 14 in a distal direction to partially or fully expose medical device 20 for delivery in system 10. In some embodiments, movement of capsule 14 can be automatically or manually actuated.

Figure 3:
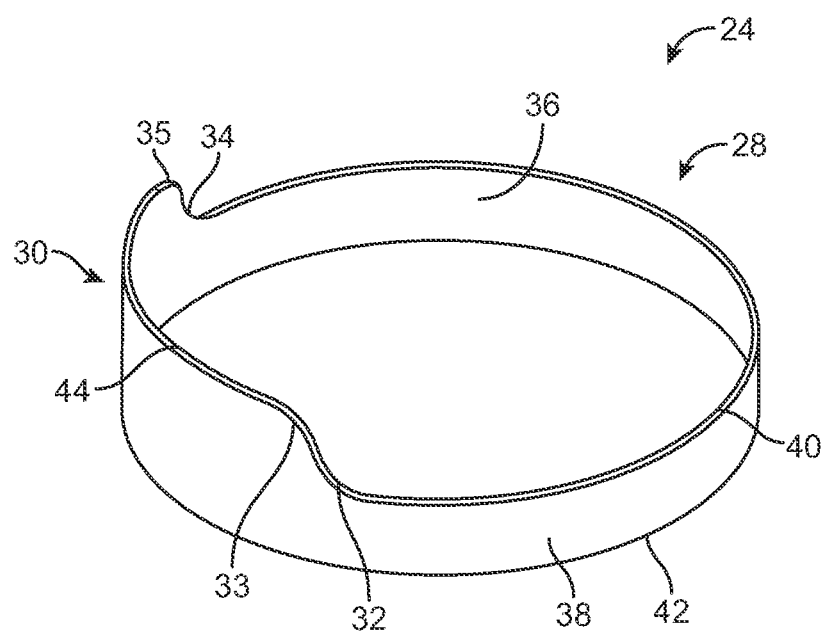
FIG. 3 illustrates a front perspective view of an embodiment of a marker band for use in the delivery system of FIG. 1.

FIG. 3 illustrates a front perspective view of marker band 24. Marker band 24 includes a band portion 28 and indicator 30 in the form of a protrusion extending from band portion 28 in a distal direction. Band portion 28 can be in the form of a continuous ring. Indicator 30 can be configured to allow the rotational orientation of marker band 24 to be determined while medical device 20 is within vasculature 12. For example, the rotational orientation of medical device 20 can be determined with respect to a central axis of vasculature 12. In some embodiments, at least a portion of marker band 24 can include a radiopaque material. Certain radiopaque materials may be viewed using a fluoroscope to determine the radial alignment marker band 24, medical device 20, and/or capsule 14 while medical device 20 is within vasculature 12. In some embodiments, delivery system 10 can, for example, incorporate spines to encourage system 10 to bend and orient with vasculature 12. Indicator 30 can be aligned 90 degrees offset from the capsule spine. Such an offset can allow a viewer to determine which side of the capsule is contacting a vasculature wall or other anatomy. In some cases, by preferentially orienting the medical device into the delivery system during the loading process, the probability of a desired delivery orientation can be increased.

Marker band 24 can include corners 32, 33, 34, and 35 between indicator 30 and band portion 28. These corners can be substantially rounded, for example with a fillet of approximately 0.02 inches. In some embodiments, one or all of corners 32, 33, 34, and 35 can be squared, chamfered, or another desired shape.

Marker band 24 can include a substantially smooth inner sidewall 36 and a substantially smooth outer sidewall 38. Marker band 24 can include a substantially flat first surface 40, a substantially flat second surface 42, and a substantially flat third surface 44. In some embodiments, the length from first surface 40 to second surface 42 can range from about 0.020 inches to about 0.030 inches. In some embodiments, the length from second surface 42 to third surface 44 can range from about 0.045 inches to about 0.060 inches. Suitable larger or smaller dimensions can be used.

In some embodiments, indicator 30 protrudes from band portion 28. The indicator can protrude from band portion 28 a distance ranging from about 1.0 mm to about 10 mm or longer. In some embodiments, indicator 30 can protrude a distance ranging from about 1.0 mm to about 4.3 mm.

Figure 4:
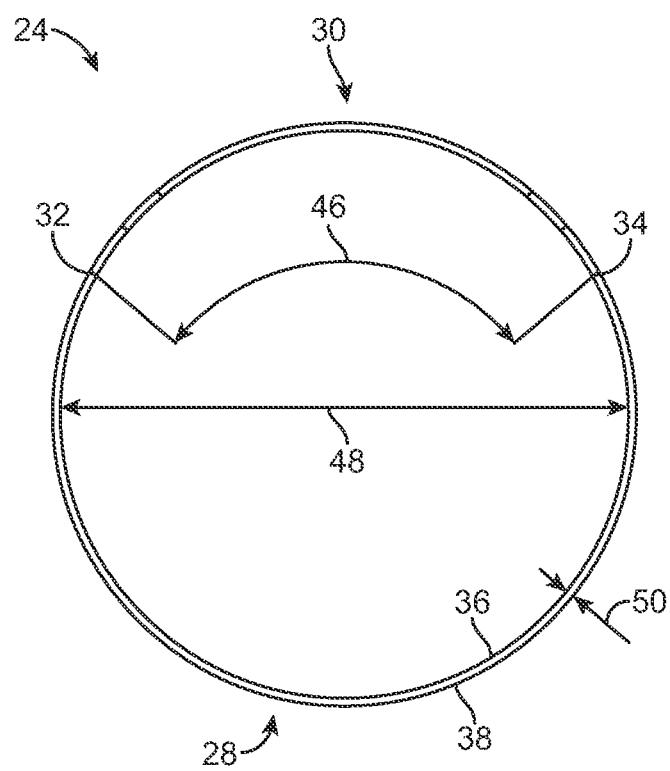
FIG. 4 illustrates a top view of the marker band of FIG. 3.

FIG. 4 illustrates a top view of marker band 24. Angle 46 between corner 32 and corner 34 of indicator 30 can be approximately 100 degrees. The inner diameter 48 of marker band 24 can be approximately 0.216 inches. Thickness 50 between inner sidewall 36 and outer sidewall 38 can be approximately 0.0025 inches.

Figure 5:
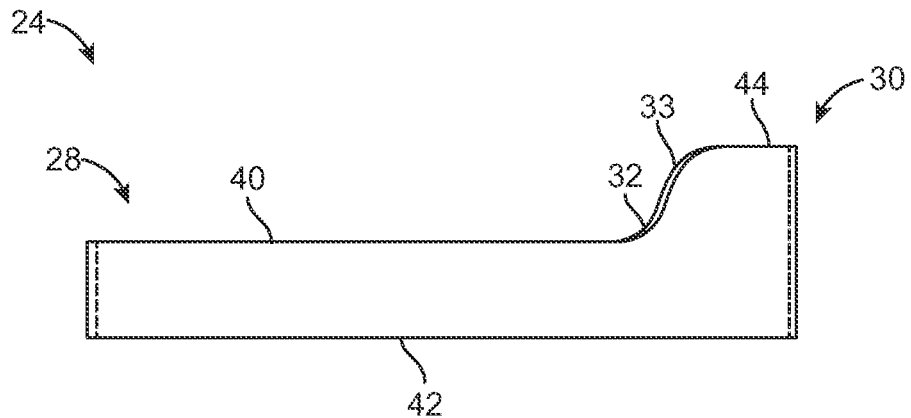
FIG. 5 illustrates a side view of the marker band of FIG. 3
Figure 6:
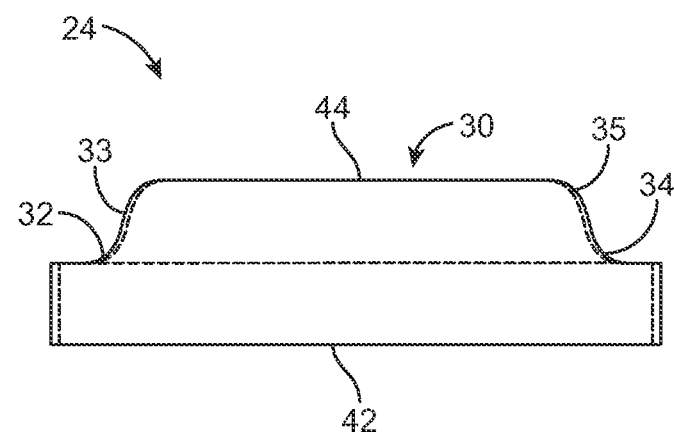
FIG. 6 illustrates another side view of the marker band of FIG. 3.
Figure 7:
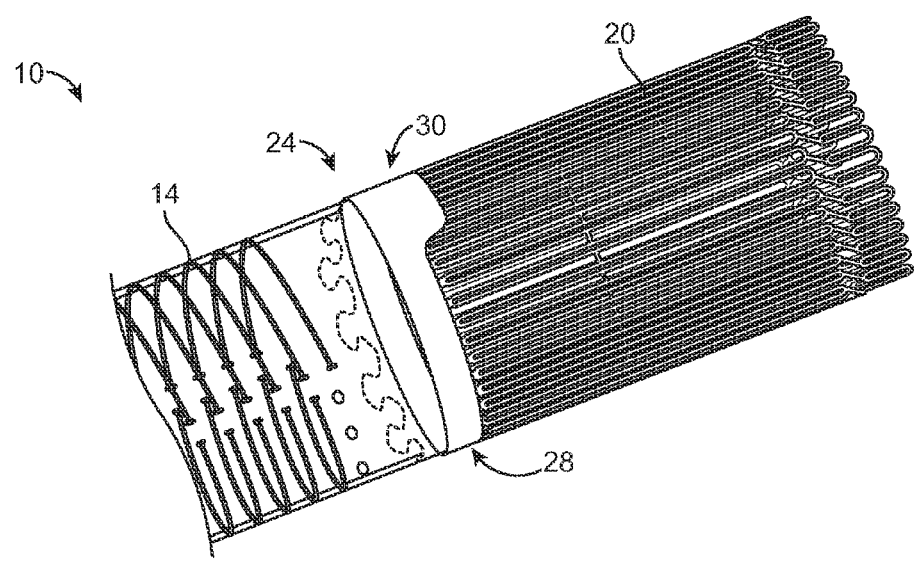
FIG. 7 illustrates a portion of a delivery system including the marker band of FIG. 3.

FIGS. 5-7 illustrate various views of marker band 24. Specifically, FIG. 5 illustrates a first side view of marker band 24. FIG. 6 illustrates a second side view of marker band 24 that is rotated 90 degrees relative to the side view of FIG. 5. FIG. 7 illustrates a front perspective view of a portion of delivery system 10 including capsule 14, medical device 20 and marker band 24.

A method for determining a rotational orientation of delivery system 10 for delivering medical device 20 through vasculature 12 can include providing delivery system 10 including capsule 14 and marker band 24 rotatably fixed to capsule 14. Marker band 24 can include indicator 30 configured to allow rotational orientation of marker band 24 to be determined while capsule 14 is in vasculature 12.

The method can further include delivering medical device 20 through vasculature 12 and determining a rotational orientation of marker band 24 while capsule 14 is in vasculature 12. The rotational orientation can be determined with respect to a central axis of vasculature 12. In some embodiments, the act of determining the rotational orientation of marker band 24 while medical device 20 is in vasculature 12 includes using a fluoroscope to view indicator 30 of marker band 24. In some embodiments, the method further includes adjusting the rotational orientation of marker band 24 in response to the determined rotational orientation.

Figure 8:
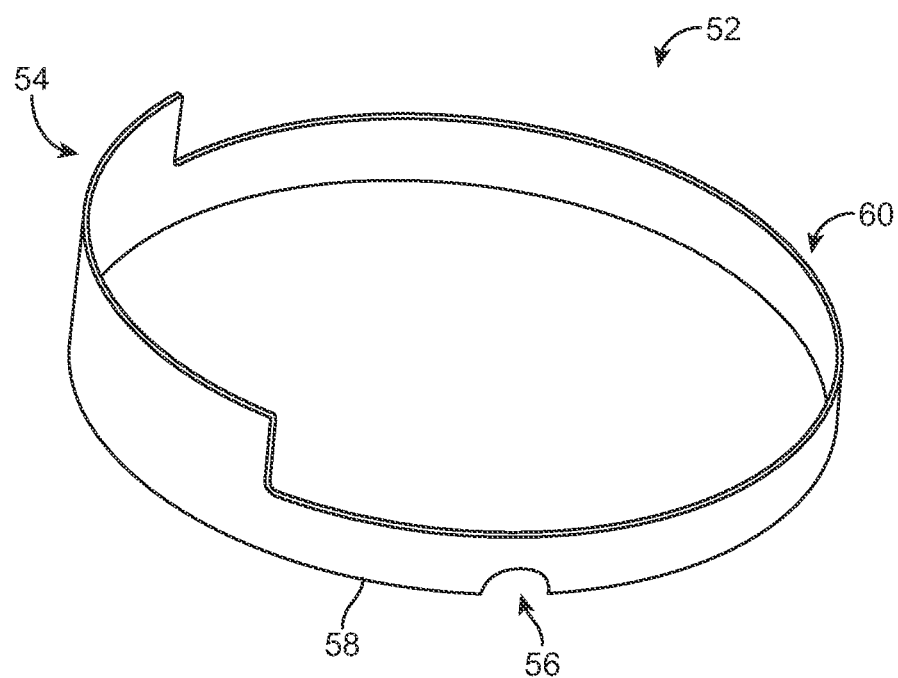
FIG. 8 illustrates a front perspective view of another embodiment of a marker band for use in the delivery system of FIG. 1.

FIG. 8 illustrates an alternative embodiment of a marker band 52. Marker band 52 includes an indicator 54 similar in function to indicator 30 of FIG. 3. Marker band 52 further includes a notch 56 formed within surface 58 of a band portion 60 of marker band 52. Notch 56 can assist with orientation during welding or assembly. Notch 56 can further or alternatively assist with fixturing to align with a spine of capsule 14. In some embodiments, notch 56 can be positioned at another suitable location on marker band 52. In some embodiments, marker band 52 can include a plurality of notches 56.

As described further herein, other configurations for indicators may be suitable. Indicators can, for example, be in the form of suitable extensions, protrusions, asymmetrical feature, and/or cut-out pattern, which can provide the user a sense of directionality or orientation within the body. For example, an indicator can protrude from a band portion and can be in the form of a long and narrow protrusion. A marker band can include a plurality of asymmetrical indicators that can, for example, allow the rotational orientation of the marker band to be determined while the medical device is delivered through a vasculature.

Figure 9:
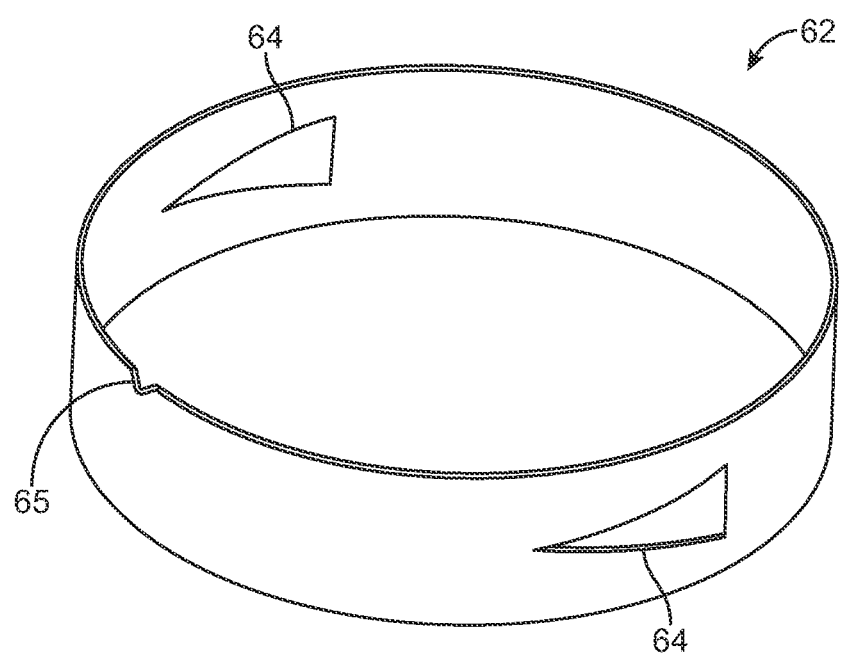
FIG. 9 illustrates a front perspective view of another embodiment of a marker band for use in the delivery system of FIG. 1.
Figure 10:
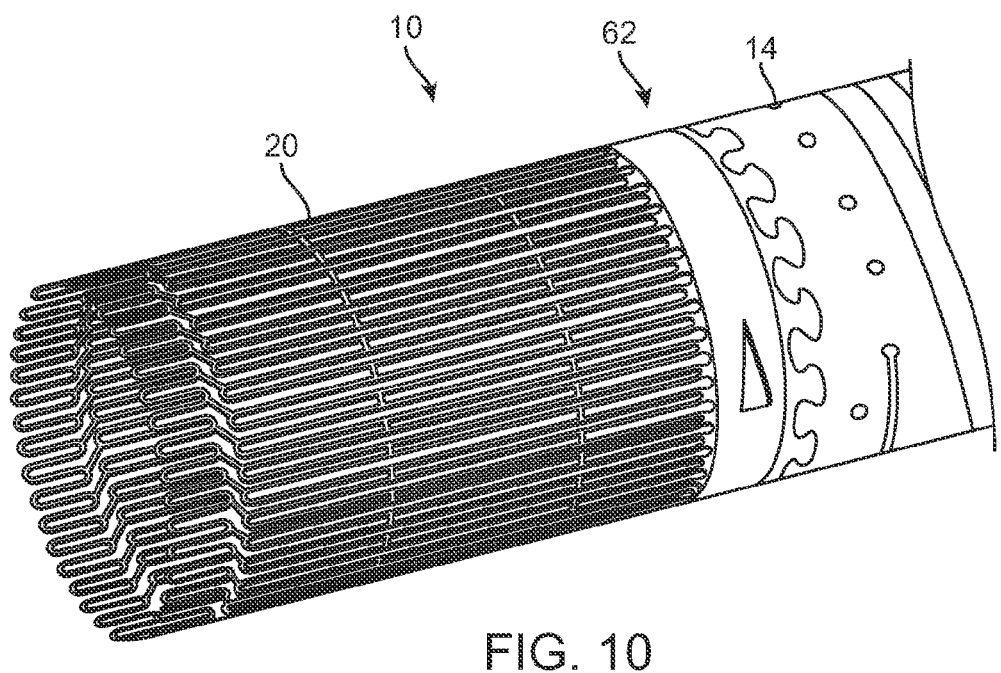
FIG. 10 illustrates a portion of a delivery system including the marker band of FIG. 9.

For example, FIG. 9 illustrates another embodiment of a marker band 62. Marker band 62 can include an indicator 64 in the form of an opening within marker band 62. Indicator 64 can be centered within the marker band. Indicator 64 can be in the form of a geometric shape. For example, indicator 64 can be in the shape of a triangle that indicates the orientation of marker band 62. The base of the triangle of indicator 64 can be approximately 0.027 inches+/−0.001 inches. The height of the triangle of indicator 64 can be approximately 0.066 inches+/−0.001 inches. Marker band 62 includes two indicators 64, but can include any suitable number of indicators 64. In some embodiments, indicators 64 can have different shapes, orientations, and/or sizes. In some embodiments, marker band 62 can include a notch 65 similar to other notches described herein. FIG. 10 illustrates a front perspective view of a portion of delivery system 10 including capsule 14, medical device 20 and marker band 62.

Figure 11:
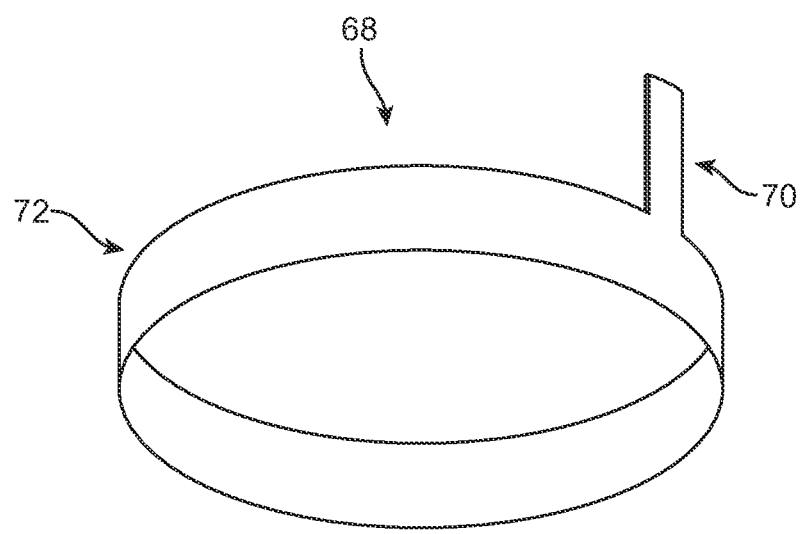
FIG. 11 illustrates a front perspective view of another embodiment of a marker band for use in the delivery system of FIG. 1.
Figure 12:
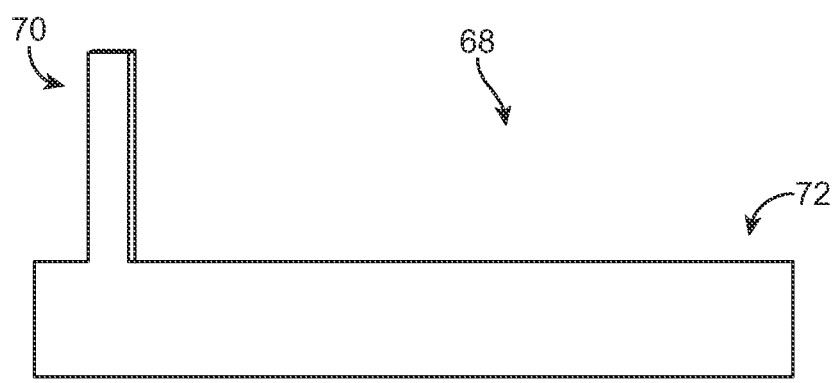
FIG. 12 illustrates a side view of the marker band of FIG. 11.

FIGS. 11-12 illustrate various views of another embodiment of a marker band 68. In particular, FIG. 11 illustrates a front perspective view of marker band 68 and FIG. 12 illustrates a side view of marker band 68. Marker band 68 can include an indicator 70 in the form of a narrow protrusion. Indicator 70 can be positioned on capsule to face in a distal direction or a proximal direction, as desired. The length of indicator 70 can be designed to avoid bending in a flare region of capsule 14. For example, the length of indicator 70 can be determined with reference to the distance from base portion 72 to the tip of the distal end of capsule 14. For example, the length can be designed to be not more than about 45% of the distance from the marker band to the distal end of capsule 14. For example, if the distance from the marker band is about 11.3 mm, the length of indicator 70 can be designed to be approximately 5 mm.

Figure 13:
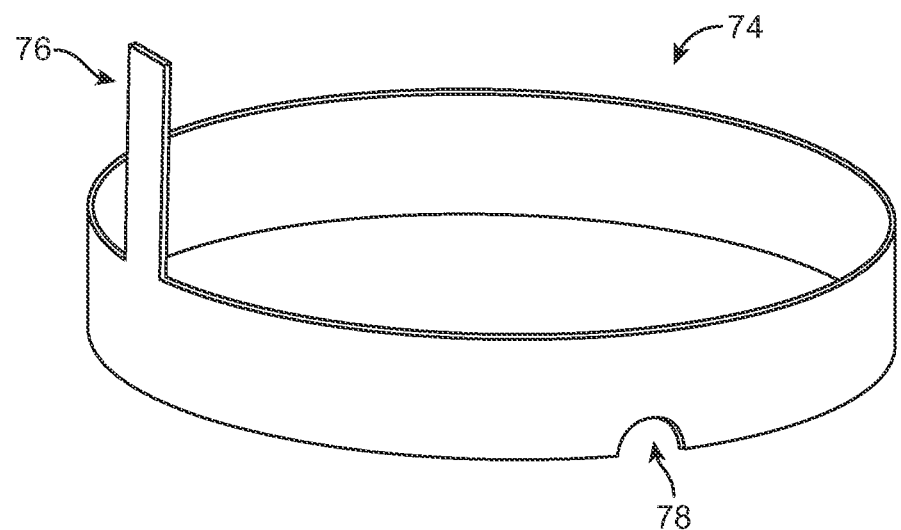
FIG. 13 illustrates a front perspective view of another embodiment of a marker band for use in the delivery system of FIG. 1.

FIG. 13 illustrates another embodiment of marker band 74 including an indicator 76 and a notch 78, which can be similar in function to other indicators and notches described herein.

Figure 14:
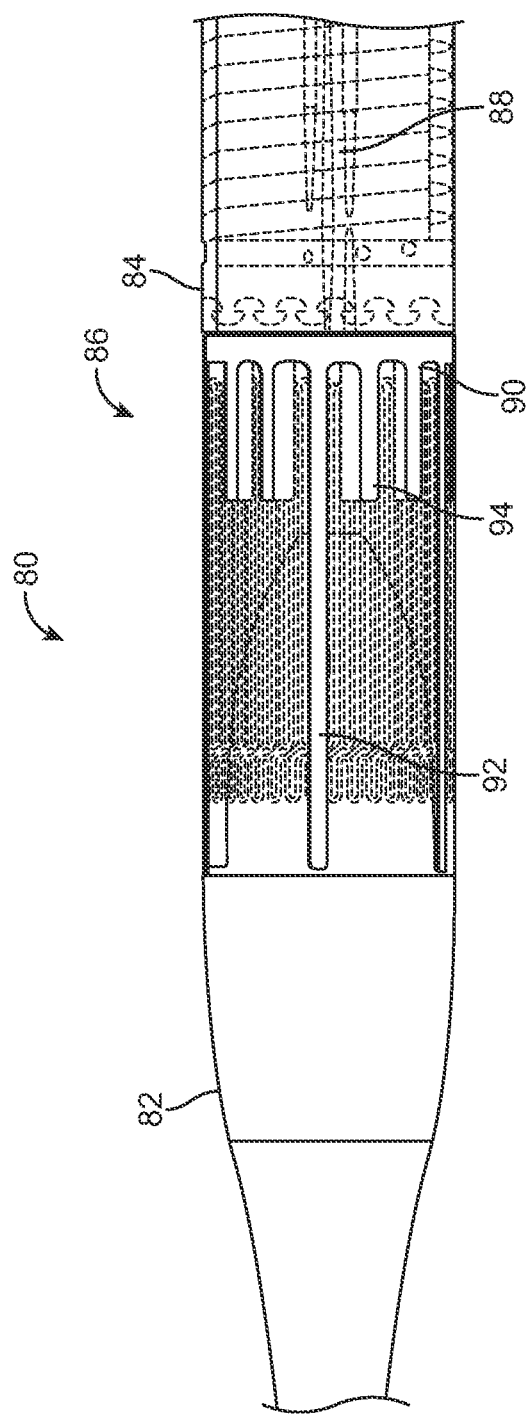
FIG. 14 illustrates a portion of another embodiment of a delivery system in accordance with one embodiment of the present invention.
Figure 15:
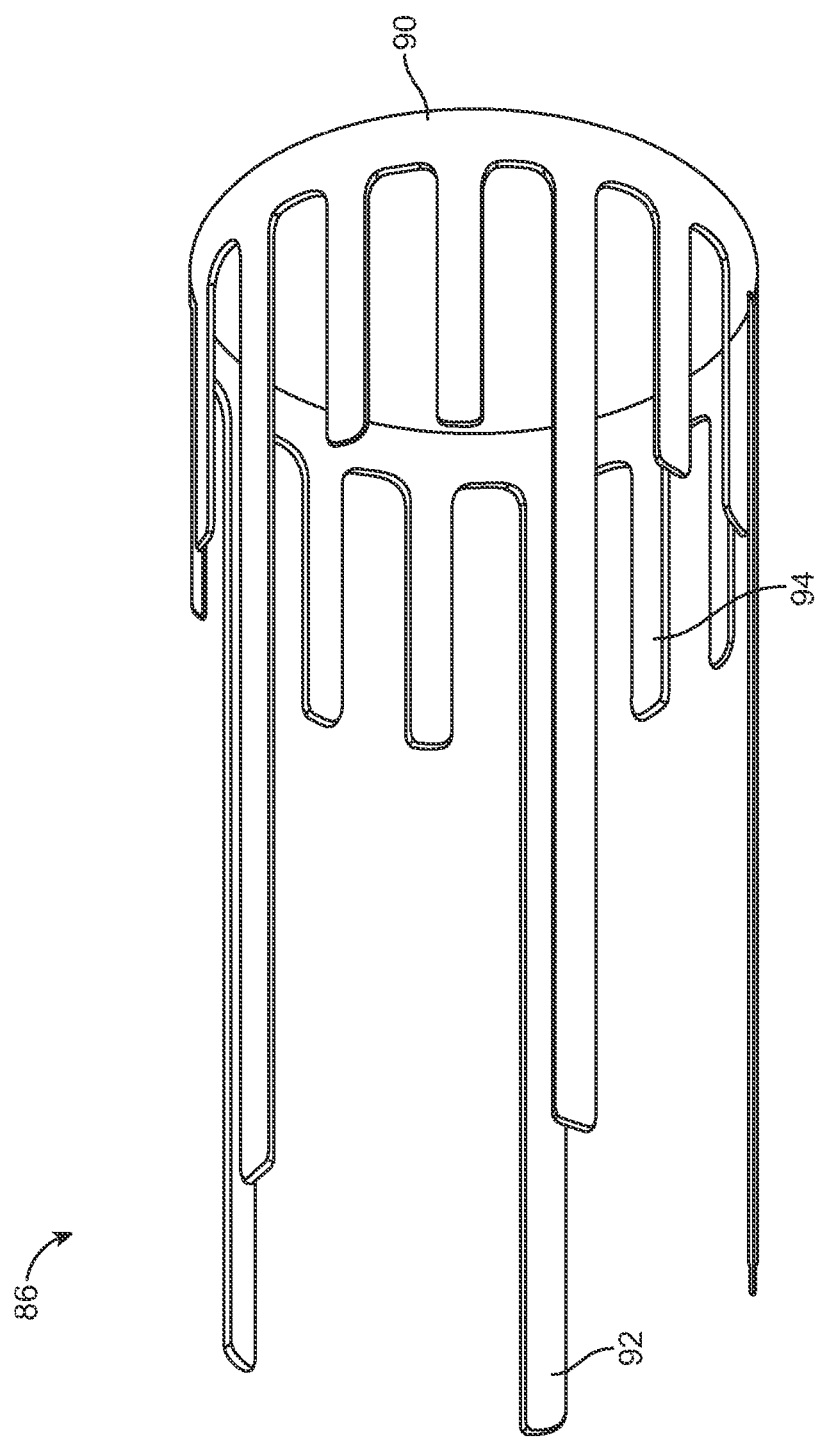
FIG. 15 illustrates a front perspective view of an embodiment of a marker band for use in the delivery system of FIG. 14.
Figure 16:
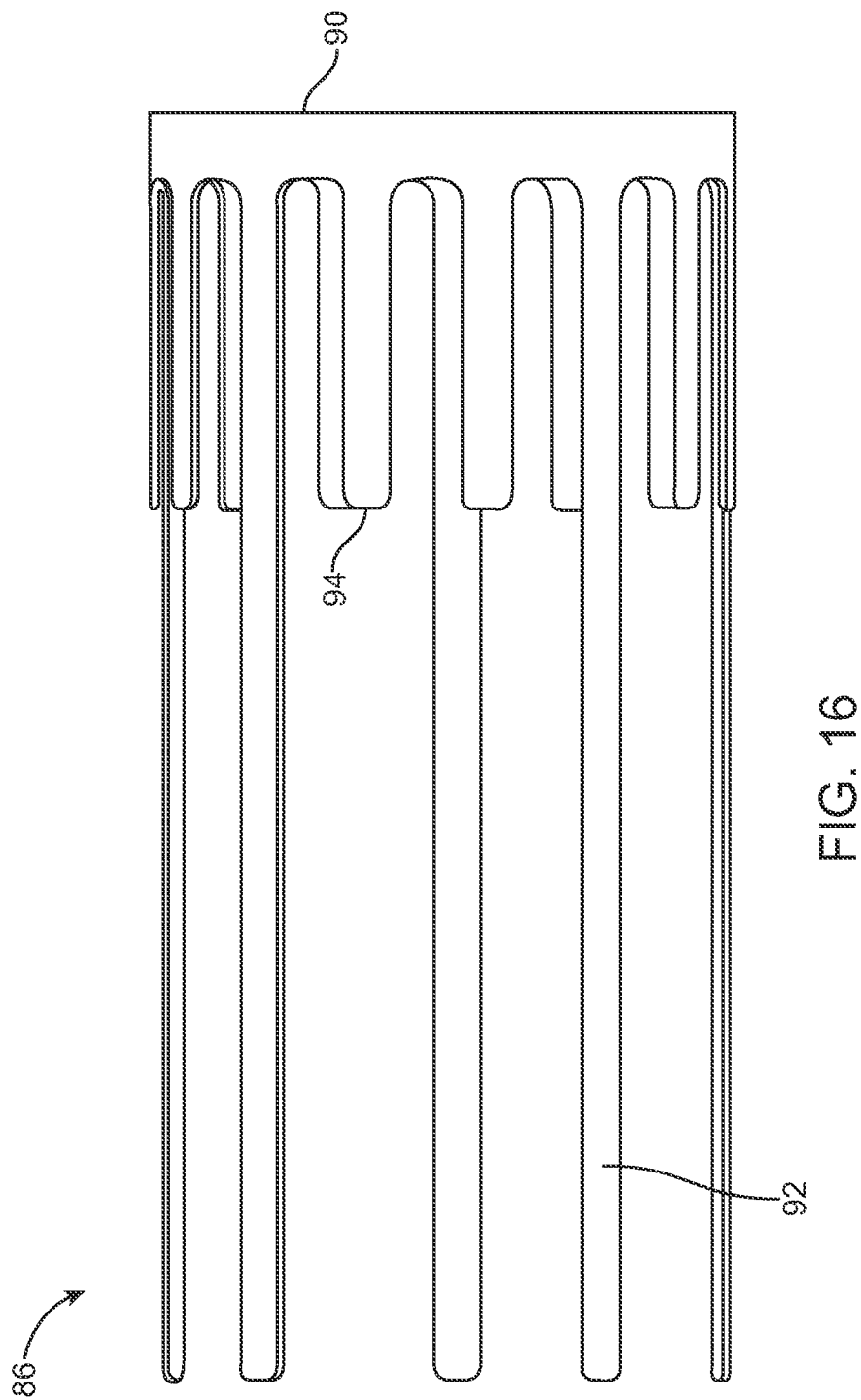
FIG. 16 illustrates a side view of the marker band of FIG. 15.

FIGS. 14-16 illustrate various views of another embodiment of marker band 86. In particular, FIG. 14 illustrates a delivery system 80 for delivering medical device 20 through vasculature 12 including marker band 86. FIG. 15 illustrates a front perspective view of marker band 86. FIG. 16 illustrates a side view of marker band 86. System 80 includes a dilator 82, a capsule 84, a marker band 86, and a medical device 88. One or more of these components can be similar in function to other components described herein. Marker band 86 can be attached to a proximal end of capsule 84 and can include a base portion 90 and one or more protrusions 92, 94 extending from base portion 90 in a distal direction. In some embodiments, protrusion 92 can be configured to extend to a distal end of capsule 84. The distal end of protrusion 92 can form an expandable section, which can allow marker band 86 to be partially placed over a flaring section of capsule 84 without substantially interfering with the ability of capsule 84 to flare outwards. In some embodiments, such a configuration can allow a user to determine when the medical device has been fully recaptured by capsule. In some cases, this can be important because if the medical device is recaptured too much or too little, the delivery system may be damaged and/or the patient may be harmed.

Base portion 90 can be in the form of a ring, such as for example, a non-expandable solid ring. In some embodiments, base portion 90 can be configured to attach to capsule 84 of delivery system 80. Base portion 90 can be positioned at the distal end of capsule 84. Like other marker bands described herein, marker band 86 can include an indicator that allows a rotational orientation of marker band 86 to be determined while the medical device is in the vasculature. In some embodiments, one or more of protrusions 92 and 94 can be configured to function as such an indicator.

As described above, marker band 86 can include protrusions 92 and 94 that extend distally from the base portion. The protrusions can, for example, be in the form of narrow fingers that are laser cut into the marker band. Protrusions 92 and 94 can be configured to expand with the flare portion of the capsule. The protrusions can be the same or different lengths. In some embodiments, marker band 86 can include two sets of protrusions having two distinct lengths. For example, one set of protrusions 92 can correspond to the distal end of capsule 84 and another set of protrusions 94 can correspond to the distal end of medical device 88.

The choice of materials for the various valve prostheses described herein can be informed by the requirements of mechanical properties, temperature sensitivity, biocompatibility, moldability properties, or other factors apparent to a person having ordinary skill in the art. For example, one more of the parts (or a portion of one of the parts) can be made from suitable plastics, such as a suitable thermoplastic, suitable metals, and/or other suitable materials. One or more components or portions of components can be made of the same or similar material as any other component. One or more components or portions of components can be configured such that they are more flexible than another component or portion of a component. In some embodiments, one or more components can include radiopaque materials.

In some embodiments, one or more components can include additional and/or embedded structure configured to provide increased mechanical strength while allowing for increased flexibility. In some embodiments, one or more components, such as for example the capsule can include a metal laser cut tube, a wound coil, braid, or other suitable structure for increasing mechanical strength. The marker band can be made of 0.007 inch WT Ni-Ti flare tubing, for example.

In some embodiments, one or more components can be entirely or partially constructed using a single material or a composite material and/or a multi-layer material. In some embodiments, one or more of the components can include a material with a low coefficient of friction. For example, one or more portions of the systems, such as an exterior of a capsule can be coated with a biocompatible lubricant. In some embodiments, such a material can, for example, assist in the delivery system, delivering a medical device and/or withdrawing the system from a body lumen. In some embodiments, one or more components can include a multi-layer design, including for example one or more layers can be made entirely or partially of polymer. In some embodiments, one or more layers can be made entirely or partially of high-density polyethylene (HDPE). In some embodiments, one or more layers can be made entirely or partially of polytetrafluoroethylene (PTFE).

The foregoing description of the invention has been presented for purposes of illustration and description. It is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

The invention claimed is:

1. A method for determining a rotational orientation of a delivery system for a medical device through a vasculature, the method comprising:

receiving a delivery system including a capsule and a marker band rotatably fixed to the capsule, the marker band including a single band portion disposed at a proximal end of the capsule and a plurality of protrusions extending distally from the band portion, wherein at least one of the plurality of protrusions extends to a distal end of the capsule and wherein at least one of the plurality of protrusions does not extend to the distal end of the capsule, wherein the plurality of protrusions are configured to allow rotational orientation of the marker band to be determined while the capsule is in the vasculature;

delivering the medical device through the vasculature;

determining a rotational orientation of the marker band while the capsule is in the vasculature, the rotational orientation being around a central axis of the vasculature.

2. The method of claim 1, wherein the marker band includes a radiopaque material, and
wherein the act of determining the rotational orientation of the marker band while the medical device is in the vasculature includes using a fluoroscope to view the marker band.

3. The method of claim 1, further comprising:
adjusting the rotational orientation of the capsule in response to the determined rotational orientation.

4. The method of claim 1, wherein the vasculature is a human aorta.

5. A delivery system for delivering a medical device through a vasculature, the system comprising:
a capsule for housing the medical device during delivery; and
a marker band attached to the capsule,
wherein the marker band includes a base portion disposed at a proximal end of the capsule and a plurality of protrusions extending from the base portion towards a distal end of the capsule, wherein it least one of the protrusions extends to a distal end of the capsule and wherein at least one of the plurality of protrusions does not extend to the distal end of the capsule.

6. The delivery system of claim 5, wherein the marker band is made of radiopaque material.

7. The delivery system of claim 5, wherein the base portion is in the form of a single continuous ring, and
wherein the protrusions protrude from the base portion and are in the form of narrow protrusions, and wherein the at least one protrusion extending to the distal end of the capsule is a long and narrow protrusion.

8. The delivery system of claim 5, wherein a plurality of the plurality of protrusions extend from the base portion to the distal end of the capsule.

9. The delivery system of claim 5, wherein the marker band includes an indicator that allows a rotational orientation of the marker band to be determined while the medical device is in the vasculature, rotational orientation being around a central axis of the vasculature.

10. The delivery system of claim 5, wherein the plurality of protrusions includes a plurality of long protrusions extending from the base portion to the distal end of the capsule and a plurality of short protrusions extending from the base portion, wherein each of the plurality of short protrusions is shorter than each of the plurality of long protrusions.

11. The delivery system of claim 10, wherein at least one of the plurality of short protrusions is disposed between an adjacent pair of the long protrusions.

12. The delivery system of claim 10, wherein a plurality of short protrusions are disposed between each adjacent pair of the long protrusions.

13. The delivery system of claim 5, wherein the plurality of protrusions are configured to allow the capsule to flare outwardly.

14. The delivery system of claim 1, wherein the plurality of protrusions are configured to allow the capsule to flare outwardly.

* * * * *